United States Patent [19]

Voorhees et al.

[11] Patent Number: 5,266,307
[45] Date of Patent: Nov. 30, 1993

[54] RETINOIC ACID AS A SKIN TANNING AGENT IN PERSONS OF LIGHT SKIN COLOR

[75] Inventors: John J. Voorhees; Christopher E. M. Griffiths; Charles N. Ellis, all of Ann Arbor, Mich.

[73] Assignee: The Regents of the University of Michigan, Ann Arbor, Mich.

[21] Appl. No.: 861,138

[22] Filed: Mar. 31, 1992

[51] Int. Cl.$^5$ ........................... A61K 7/42; A61K 7/48
[52] U.S. Cl. ....................................... 424/59; 514/725; 514/844; 514/847; 514/944
[58] Field of Search ........................... 424/59; 514/725

[56] References Cited

U.S. PATENT DOCUMENTS 4,108,880  8/1978  Gander et al. .................... 424/59
5,039,513  8/1991  Chatterjee et al. .

OTHER PUBLICATIONS

Nair et al, *J. Invest. Dermatol.*, vol 92 (1989).

*Primary Examiner*—Dale R. Ore
*Attorney, Agent, or Firm*—Oblon, Spivak, McClelland, Maier & Neustadt

[57] ABSTRACT

Topical application of retinoic acid is effective for increasing the tyrosinase activity in the skin of people having light skin. Thus, topical application of retinoic acid may be used to effect a suntan in people having light skin and as a consequence protect against photodamage.

5 Claims, No Drawings

RETINOIC ACID AS A SKIN TANNING AGENT IN PERSONS OF LIGHT SKIN COLOR

BACKGROUND OF THE INVENTION

1. Field of the Invention:

The present invention relates to a method for effecting a suntan on people of light skin by applying retinoic acid to the skin.

2. Discussion of the Background:

In many cultures, a suntan is considered a sign of good health and beauty. In fact, sunbathing to achieve a suntan is practiced in many parts of the world. In climates and during seasons which are not conducive to outdoor sunbathing, some people resort to indoor exposure to intense ultraviolet radiation to achieve a suntan. The increased melanin which is part of the suntan is probably protective of photodamage and maybe skin cancer.

However, prolonged exposure to natural sunlight or other excessive UV radiation is know to have many serious detrimental effects. These detrimental effects are discussed in, e.g., U.S. Pat. No. 5,039,513, which is incorporated herein by reference. Specifically, the damaging effects caused by excessive sunlight or UV exposure include, erythema (i.e., sunburn) and skin cancer.

Retinoic acid is known to result in the lightening of liver spots associated with photodamage (Rafal, E.S., *New Engl. J. Med.*, vol. 326, pp. 368-374 (1992)).

However, there remains a need for a method for effecting a suntan in people of light skin color, which does not involve excessive exposure to natural sunlight or other sources of ultraviolet radiation and does not suffer from the disadvantages arising from such exposure.

SUMMARY OF THE INVENTION

Accordingly, one object of this invention is to provide a novel method for effecting a suntan on people of light skin color.

It is another object of the present invention to provide a novel method for effecting a suntan on people of light skin color which does not require or involve exposure to natural sunlight or other sources of ultraviolet radiation.

These and other objects, which will become apparent during the following detailed description, have been achieved by the inventors' discovery that applying retinoic acid to the skin of people of light skin color results in the darkening of the skin.

DETAILED DESCRIPTION OF THE PREFERRED EMBODIMENTS

Thus, the present invention provides a method for effecting a suntan on the skin of people of light skin color. By the term "effecting a suntan" is meant the darkening of the skin. Such darkening of the skin may be measured quantitatively as an increase in the melanin content in the skin which is related to an increase in the tyrosinase activity in the skin. Accordingly, the present invention provides a method for increasing the melanin content of the skin and increasing the activity of tyrosinase in the skin.

As noted above the present method involves applying retinoic acid to the skin. Retinoic acid is a known compound of the formula:

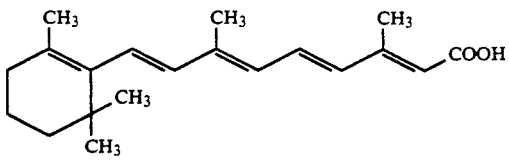

The preparation of retinoic acid is described in U.S. Pat. No. 3,006,939, and Lakshmanan et al, *Biochem. J.*, vol. 90, p. 569 (1964), and the structure has been confirmed by x-ray crystallography by Stam et al, *Acta Cryst.*, vol. 16, p. 62 (1963), all of which are incorporated herein by reference. The properties of retinoic acid are reviewed in Dowling et al, *Vitam. Horm.*, vol. 18, p. 515 (1960), incorporated herein by reference.

In the present method, the retinoic acid is administered by applying a composition containing the retinoic acid directly to the skin to be treated. The composition, which will be described below, is suitably applied in an amount such that the retinoic acid is applied to the skin in an amount of 0.5 to 10 mg/cm$^2$ of skin, preferably 1 to 5 mg/cm$^2$ of skin, which is to be treated.

The application of the retinoic acid composition to the skin is preferably carried out in a repetitive fashion. Thus, it is preferred that the composition be applied from 3 to 7 times per week, more preferably 7 times per week. Especially good results have been obtained when the retinoic acid composition is applied to the skin on a daily basis. It is particularly preferred that the retinoic acid be applied in the evening immediately after washing and drying the skin.

The repeated application of the retinoic acid containing composition is suitably carried out over a period of time sufficient to result in an amelioration of the hyperpigmentation. Thus, the treatment is typically carried out for a time of 4 to 40 weeks, more typically 4 to 20 weeks.

It may be advantageous, when carrying out the treatment over a period of weeks or months, to start the treatment with an initial dosage of 0.05 to 1 mg/cm$^2$ of skin, preferably 0.1 to 0.5 mg/cm$^2$ of skin, and then gradually increase the dosage to 0.5 to 10 mg/cm$^2$ of skin, preferably 1 to 5 mg/cm$^2$ of skin as the patient becomes acclimated to the treatment. If, during the treatment, the patient develops any irritation due to the retinoic acid, it may be advantageous to discontinue the treatment for 1 to 4 days, preferably 1 to 2 days, or until the irritation subsides.

In the present method, the retinoic acid is preferably applied to a person having light skin. By the term "a person having light skin" is meant a person who has a skin type between 1 to 3 (Fitzpatrick skin type).

As noted above, the retinoic acid is suitably applied to the skin in the form of a composition. The only requirement with regard to the concentration of the retinoic acid in the composition is that the retinoic acid must be present in an amount such that the desired rate of application of retinoic acid may be achieved by convenient application of the composition to the skin. Thus, the concentration of retinoic acid in the composition is suitably 0.025 to 0.2 wt.%, preferably 0.05 to 0.1 wt.%, most preferably about 0.1 wt. % based on the total weight of the composition.

The composition may take any form which is suitable for application to human skin. Thus, the composition may be in the form of an oil, ointment, cream, lotion, gel, etc. The composition may contain, as additional ingredients, water, oil, alcohols (such as ethanol, isopropanol, or propanol), emulsifying agents, perfumes, coloring agents, fillers, abrasive agents, moisturizers, etc. Especially good results have been achieved using 0.1% Retin-A ® Cream (product of Ortho Pharmaceutical Corporation, Raritan, N.J.).

Thus, the inventors have discovered that application of retinoic acid to the skin of people of light skin color is effective for darkening the skin. Retinoic acid is a modulator of many cellular activities. The modulation by retinoic acid occurs in a cell in a way that is defined by the context of the physiology of the cell at the time the retinoic acid is applied. A typical example of this is that when there is heightened activity in a cell, retinoic acid reduces the activity and when the activity in question is low, retinoic acid elevates the activity. The inventors have noted that the skin of darkly pigmented (black) individuals as well as liver spots in white (caucasian) individuals is reduced by retinoic acid. That is to say, black skin and liver spots are lightened or caused to disappear entirely by retinoic acid.

Retinoic acid has now been applied topically for four days in white individuals and it has been found that there is an augmentation in tyrosinase (the pigment forming enzyme) activity in four days. In this four day test, there was no observed increase pigment, because the time was too short. However, because this enzyme (tyrosinase) is responsible for the formation of pigment, if the retinoic acid were applied for several weeks to several months, melanin pigment would accumulate and cause tanning. This pathway of pigmentation is well accepted in the scientific community. Furthermore, white patients have been treated in the clinic with retinoic acid and it has been anecdotally noted that some of them to develop a mild tanned appearance as a result of the drug. This increased tyrosinase activity is described both biochemically and histochemically more fully below.

Other features of the invention will become apparent in the course of the following descriptions of exemplary embodiments which are given for illustration of the invention are not intended to be limiting thereof.

EXAMPLES

Tyrosinase activity is a key determinant of melanin production in skin. As retinoic acid (RA) regulates tyrosinase activity in melanoma cells, the modulation of pigmentation in vivo by RA was analyzed. The following parameters in keratome biopsies from black and white subjects treated with nothing, vehicle (VEH), RA (0.1%) and the irritant sodium isuryl sulfate (SLS) 2% for 4 days under occlusion were assessed: tyrosinase activity biochemically and histochemically (DOPA reaction); tyrosinase steady state mRNA levels by Northern blot analysis and semi-quantitative PCR; melanin content by spectrophotometry. In untreated skin, tyrosinase activity was 132% higher ($p<0.0001$, $n=20$), and melanin content was 22% higher ($p<0.0001$, $n=20$) in blacks versus whites. Four days of RA treatment did not alter tyrosinase activity or melanin content in black skin. In contrast, RA treatment significantly induced tyrosinase activity (173% increase, $n=8$, $p=0.01$) in white skin. However, melanin content was not increased during four days of RA treatment. Tyrosinase activity was increased 24% ($p=0.5$, $n=7$) in SLS treated skin and 76% ($p=0.003$, $n=7$) in RA treated skin when both are compared to VEH treated skin. The RA effect could be differentiated from non-specific irritation, since tyrosinase activity in RA treated skin was significantly greater (43%) than in SLS treated skin ($p=0.01$, $n=7$). Similar results were obtained with the DOPA reaction assay (melanocyte numbers, staining intensity and dendricity) done on VEH, SLS and RA treated white skin ($n=12$). Northern blot analysis ($n=3$) and semi-quantitative polymerase chain reaction ($n=6$) demonstrated that RA treatment did not alter tyrosinase mRNA levels in white skin, indicating that the induction of tyrosinase in vivo apparently does not involve increased gene expression at this four day time point. These data show: low tyrosinase activity in white skin in vivo is RA inducible; high tyrosinase activity in black skin in vivo is neither further induced nor reduced by RA. High tyrosinase activity and melanin content in black versus white skin and RA inducibility of tyrosinase in white skin raise the possibility that long-term RA treatment may increase melanin content of white skin.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by letters patient of the United States is:

1. A method for effecting a suntan in a person having light skin, comprising applying to said skin an effective amount of retinoic acid.

2. The method of claim 1, wherein said effective amount is 0.5 to 10 mg/cm² of skin which is treated.

3. The method of claim 2, wherein said effective amount is 1 to 5 mg/cm² of skin which is treated.

4. The method of claim 1, wherein said applying is carried out from 3 to 7 times per week.

5. The method of claim 4, wherein said applying is carried out daily.